United States Patent [19]

Grisar et al.

[11] 4,126,611

[45] Nov. 21, 1978

[54] SUBSTITUTED CYCLOALKYL LACTAMIMIDES

[75] Inventors: Johann M. Grisar; Thomas R. Blohm; Edward M. Roberts, all of Cincinnati, Ohio

[73] Assignee: Richardson-Merrell Inc., Wilton, Conn.

[21] Appl. No.: 877,663

[22] Filed: Feb. 14, 1978

Related U.S. Application Data

[60] Division of Ser. No. 386,995, Aug. 9, 1973, which is a continuation-in-part of Ser. No. 143,259, May 13, 1971, abandoned.

[51] Int. Cl.$^2$ ............... C07D 207/22; C07D 211/72; C07D 223/12; C07D 225/02
[52] U.S. Cl. ........................ 260/239 B; 546/284; 546/304; 546/312; 546/223; 546/213; 260/239 BE; 260/326.5 L; 260/326.85; 260/326.9; 260/329 AM; 260/332.5; 424/244; 424/232; 424/263; 424/267; 424/274; 424/275
[58] Field of Search ...... 260/239 B, 239 BE, 326.5 L, 260/326.85, 326.9, 293.78, 296 R

[56] References Cited

U.S. PATENT DOCUMENTS 3,887,569   6/1975   Poos ........................ 260/293.78

FOREIGN PATENT DOCUMENTS 1,210,848   11/1970   United Kingdom .............. 260/239 B Primary Examiner—Alton D. Rollins
Attorney, Agent, or Firm—George W. Rauchfuss, Jr.; Eugene O. Retter

[57] ABSTRACT

Compounds possessing hypoglycemic, hypotensive, antiinflammatory, anticoagulant and diuretic activity are represented by compounds of the following formula

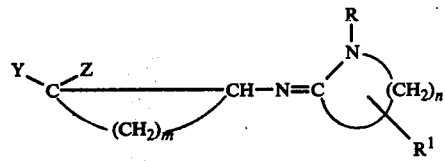

wherein Y is thienyl, cycloalkyl of from 5 to 7 carbon atoms, phenyl or substituted phenyl in which case the substituents on the substituted phenyl are selected from halogen, such as fluorine, chlorine, bromine or iodine, lower alkyl of from 1 to 4 carbon atoms and lower alkoxy of from 1 to 4 carbon atoms; Z is hydrogen or hydroxy; R is hydrogen, lower alkyl of from 1 to 4 carbon atoms, phenyl or benzyl; $R^1$ is hydrogen, lower alkyl of from 1 to 4 carbon atoms or halogen, such as chlorine, fluorine, bromine or iodine; m is from 3 to 6; and n is from 3 to 11. Pharmaceutical compositions of these compounds and their use are also disclosed.

7 Claims, No Drawings

SUBSTITUTED CYCLOALKYL LACTAMIMIDES

This is a division of application Ser. No. 386,995, filed Aug. 9, 1973 which is a continuation-in-part of application Ser. No. 143,259, filed May 13, 1971, now abandoned.

FIELD OF INVENTION

This invention relates to novel substituted cycloalkyl lactamimide compounds and pharmaceutical compositions thereof. More particularly, this invention relates to said novel compounds and compositions having hypoglycemic utility and additionally, hypotensive, anticoagulant and diuretic activity.

SUMMARY OF INVENTION

The novel compounds of this invention are represented by those having the following formula

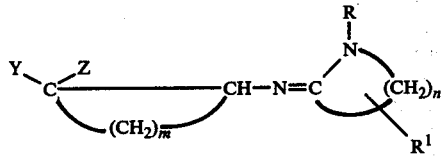

wherein Y is thienyl, cycloalkyl of from 5 to 7 carbon atoms, phenyl or substituted phenyl in which case the substituents on the substituted phenyl are selected from halogen, such as fluorine, chlorine, bromine or iodine, lower alkyl of from 1 to 4 carbon atoms and lower alkoxy of from 1 to 4 carbon atoms; Z is hydrogen or hydroxy; R is hydrogen, lower alkyl of from 1 to 4 carbon atoms, phenyl or benzyl; $R^1$ is hydrogen, lower alkyl of from 1 to 4 carbon atoms or halogen, such as chlorine, fluorine, bromine or iodine; m is from 3 to 6; and n is from 3 to 11. Also included within the scope of the invention are the pharmaceutically acceptable acid addition salts of these compounds and the individual geometric and optical isomers where applicable. Pharmaceutical compositions of said novel compounds and the administration of said compounds to a host for their biological activity are also included within the scope of the disclosed invention.

DISCUSSION OF PRIOR ART

The compounds of the present invention are novel compounds having one or more biological activities rendering them useful in the pharmaceutical arts. The closet prior art known to applicants is the compound 1-methyl-2-[(trans-2-phenylcyclopropyl)imino]pyrrolidine disclosed in Example No. 10 of French Pat. No. 1,576,111 of McNeil Laboratories published on July 25, 1969. The French patent relates only to a process for the preparation of the aforementioned and related compounds and discloses no used for said compound.

DETAILED DESCRIPTION OF INVENTION

For convenience and uniformity we have represented and named all compounds described in the disclosure as substituted 2-iminoperhydroazacarbocyclics, as represented by Formula I. It is known, however, that compounds of this type as acid addition salts may also be represented by the tautomeric form illustrated by the following Formula II:

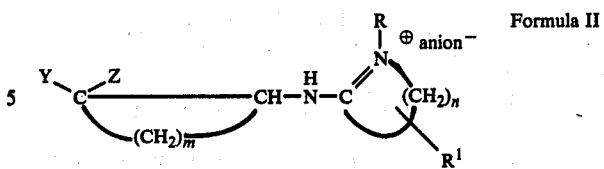

This tautomerism has been discussed by R. Kwok and P. Pranc, J. Org. Chem. 32, 740 (1967). Structures of this formula could be named differently. In solution, under the conditions of the therapeutic utility, the proportion of each tautomeric form, or the delocalization of the charge between the two nitrogen atoms, will be dependent upon numerous factors including the nature of the substituents, the pH of the medium, and the like. This equilibrium state is conveniently depicted by the following Formula III:

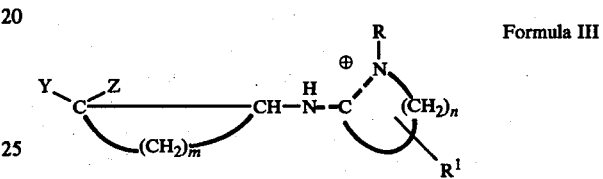

It is understood that this disclosure relates to compounds represented or named in either tautomeric form.

Preferred compounds of this invention are compounds of the following type:

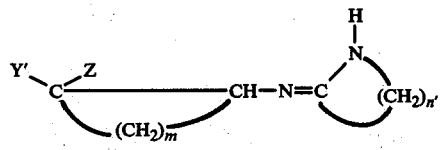

Formula IV wherein Y' is thienyl, cyclohexyl or phenyl, Z is hydrogen or hydroxy; m' is 3 to 5; and n' is 4 to 7.

As examples of the cycloalkyl radicals which the symbol Y may represent in each of the above Formulas I, II or III there may be mentioned, for example, cyclopentyl, cyclohexyl and cycloheptyl.

As examples of the lower alkyl radicals that R and $R^1$ may represent, as well as the lower alkyl radicals which may appear as substituents on the substituted phenyl radicals that the symbol Y may represent there may be mentioned, for example, methyl, ethyl, propyl and butyl. Likewise, as examples of the lower alkoxy radicals which may appear as substituents on the substituted phenyl radicals that the symbol Y may represent there may be mentioned, for example, methoxy, ethoxy, propoxy and butoxy.

As examples of compounds of this invention there may be mentioned, for example,
hexahydro-2-[(trans-2-phenylcyclopentyl)imino]azepine hydrochloride,
2-[2-({p-chlorophenyl}cyclopentyl)imino]hexahydroazepine hydrochloride,
5-tert-butylhexahydro-2-[(cis-2-phenylcyclopentyl)imino]azepine hydrochloride,
hexahydro-2-[2({o-tolyl}cyclohexyl)imino]azepine hydrochloride,
and 2-[2-({m-anisyl}cyclohexyl)imino]hexahydroazepine hydrochloride.

As examples of preferred compounds of this invention there may be mentioned, for example, hexahydro-2-[(2-phenylcyclopentyl)imino]azepine hydrochloride, hexahydro-2-[(2-phenylcycloheptyl)imino]azepine hydrochloride, 2-[(2-cyclohexylcyclopentyl)imino]hexahydroazepine hydrochloride, and most preferably the cis isomer, 2-[(2-phenylcyclopentyl)imino]piperidine hydrochloride, octahydro-2-[(2-phenylcyclopentyl)imino]azonine hydrochloride, hexahydro-2-[(2-{2-thienyl}cyclopentyl)imino]azepine hydrochloride, 2-[(2-cyclohexylcyclopentyl)imino]piperidine hydrochloride, and 2-(hexahydroazepin-2-ylidenamino)-1-phenylcyclopentanol hydrochloride.

Pharmaceutically acceptable acid addition salts of the base compounds of this invention are those of any suitable inorganic or organic acids. Suitable inorganic acids are, for example, hydrochloric, hydrobromic, sulfuric or phosphoric acids and the like. Suitable organic acids are, for example, carboxylic acids such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicyclic, 2-phenoxybenzoic and the like, or sulfonic acids such as methane sulfonic, 2-hydroxyethane sulfonic acid and the like.

It has been found that the novel compounds of this invention, including acid addition salts and individual optical and geometric isomers where applicable, possess hypoglycemic utility. In addition to their hypoglycemic utility these compounds also possess diuretic, anticoagulant and hypotensive activity. These compounds can be used in the form of pharmaceutical preparations which contain the novel compounds suitable for oral or parenteral administration. The quantity of compound in the unit dosage can vary over a wide range to provide from about 1.0 mg/kg to about 100 mg/kg of body weight of the patient per dose to achieve the desired effect. The desired hypoglycemic effect can be obtained, for example, in a 70 kg subject by consumption of 25 to 500 mg of the active ingredient taken 1 to 4 times daily.

The utility of the compounds of this invention is illustrated by the following. The compound of Example 3 demonstrated in vitro an 89% inhibition of adenosine diphosphate induced platelet aggregation in human platelet rich plasma when 100 μg of the compound was added to each milliliter of plasma. When 25 mg/kg of body weight of the compound of Example 1 was orally administered to rats the percent of urine excretion measured in milliliters was increased by 118% in 5 hours over that of a control group. When the compound of Example 19 was orally administered to rats at 100 mg/kg of body weight a 34% reduction in plasma glucose from control resulted. In a carrageenin abscess test when 500 mg/kg of body weight of the compound of Example 22 was orally administered to rats there was a decrease in abscess weight by 60%.

The compounds of this invention are prepared by reacting an excess of a lactim ether of the formula

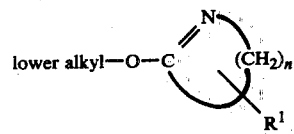

with a primary amine of the following formula

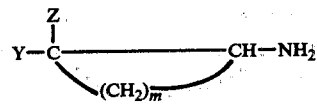

in a manner like that reported by R. E. Benson and T. L. Cairns, J. Am. Chem. Soc. 70, 2115–8 (1948). The various symbols, that is, $n$, $R^1$, Y, Z and $m$ have the meanings defined hereinbefore, and lower alkyl may be methyl, ethyl, or the like. This reaction may be carried out either in the presence or absence of a solvent. When a solvent is used it is preferred that a lower alcohol, such as, methanol, ethanol or the like be used; however, other solvents such as benzene, toluene and the like may be used. A basic or acidic catalyst such as a tertiary amine or hydrogen chloride may be added to the reaction mixture. In general it is preferred that the hydrochloride salt of the amine be used in the reaction. The temperature of the reaction can vary from −40° C. to 180° C., and the preferred temperature is about 15 to about 25° C. The reaction time varies from about 1 hour to about 60 days being dependent upon the temperature of the reaction, the reactant primary amine, and more particularly, on the degree of stearic hindrance of the amine since highly stearically hindered amines react very slowly.

The lactim ethers which find use in this reaction may be prepared from commercially available corresponding lactams by methods known in the art. For example, by reaction of an appropriate lactam with dimethyl sulfate in a solvent such as benzene, toluene, xylene or the like at the reflux temperature of the solvent for 2 to 24 hours the corresponding O-methyl lactim ether is obtained.

The amines which find use in this invention may be prepared by several known methods. The substituted cycloalkylamine may be obtained from the corresponding nitro derivative or the oxime [C. Kaiser et al., J. Med. Pharm. Chem. 5, 1243 (1962)] by reduction. Or, the cyclohexylcycloalkylamine compounds may be obtained by hydrogenation of the corresponding phenylcycloalkylamine derivative. Also by the Leuckart reaction the appropriately substituted cycloalkanone is heated with ammonium formate to a temperature of 180° to 200° C. for 2 to 12 hours to give the desired substituted cycloalkylamine. The substituted cycloalkanone derivatives may be obtained by a Grignard reaction of a suitable aryl- or cycloalkylmagnesium halide with an appropriate cycloalkanone to give the corresponding substituted cycloalkalene which is subsequently treated with hydrogen peroxide by methods generally known in the art.

The compounds of this invention may also be prepared using a complex of an appropriate lactam with phosphorus oxychloride, phosgene, borontrifluoride etherate, dimethyl sulfate, hydrogen halide or a combination of two or more such reagents. The complex formed is reacted with an appropriate primary amine described hereinabove in an aromatic hydrocarbon solvent such as benzene, toluene or xylene or an alkyl polyhalide solvent such as carbon tetrachloride, chloroform, methylene chloride, dichloroethane, tetrachloroethylene or the like. The reaction temperature is limited by the boiling point of the solvent, however, in some cases it is advantageous to carry out the reaction at room temperature or with cooling at 0° to −40° C. depending on the reactants.

EXAMPLES

Representative compounds of the invention and their preparation as well as pharmaceutical compositions and their preparation are illustrated in the following specific examples.

EXAMPLE 1

Hexahydro-2-[(cis-2-phenylcyclopentyl)imino]azepine hydrochloride

A mixture of 4.0 g of cis-2-phenylcyclopentylamine hydrochloride, M.P. 205°–206° C. and 5.0 ml of O-methylcaprolactim was allowed to stand at room temperature for 6 days with occasional stirring. A few drops of ethanol were added to maintain a stirrable slurry, after which the mixture was cooled. The resulting solid was washed with ether and recrystallized from acetone/methanol to give the desired product, M.P. 181.5°–183.5° C. (dec.).

EXAMPLE 2

Hexahydro-2-[(trans-2-phenylcyclopentyl)imino]azepine hydrochloride

Following the procedure of Example 1, only substituting for cis-2-phenylcyclopentylamine hydrochloride the appropriate molar equivalent amount of trans-2-phenylcyclopentylamine hydrochloride, M.P. 147°–149° C., the desired product was obtained, M.P. 192°–195° C.

EXAMPLE 3

2-[(cis-2-Cyclohexylcyclopentyl)imino]hexahydroazepine hydrochloride (A) Using rhodium-on-charcoal catalyst in a Paar shaker, 12.6 g of cis-2-phenylcyclopentylamine hydrochloride, M.P. 204°–206° C. in 100 ml of water was hydrogenated. In 20 hours when the theoretical amount of hydrogen had been taken up the catalyst was removed by filtration, the filtrate made basic with sodium hydroxide solution, and the resulting precipitate was extracted into ether. After evaporation of the ether the residue was distilled, B.P. 100°–102° C. (6.0 mm). The hydrochloride salt was prepared and recrystallized from isopropanolether to give 4.4 g of cis-2-(cyclohexyl)cyclopentylamine hydrochloride, M.P. 174°–176° C.

(B) By the procedure of Example 1 only employing a reaction time of 29 days and substituting for cis-2-phenylcyclopentylamine hydrochloride an appropriate amount of cis-2-cyclohexylcyclopentylamine hydrochloride, the desired product was obtained, M.P. 179°–180° C.

EXAMPLE 4

2-[(trans-2-Cyclohexylcyclopentyl)imino]hexahydroazepine hydrochloride

By the procedure described in Example 3(A) only substituting for cis-2-phenylcyclopentylamine hydrochloride an appropriate amount of trans-2-phenylcyclopentylamine hydrochloride, M.P. 142°–143° C., the hydrochloride salt of trans-2-cyclohexylcyclopentylamine was obtained, M.P. 199°–200° C. Following the procedure of Example 1 only substituting for cis-2-phenylcyclopentylamine hydrochloride an appropriate amount of trans-2-cyclohexylcyclopentylamine hydrochloride and employing a reaction time of 38 days, the desired product was obtained, M.P. 208°–210° C.

EXAMPLE 5

2-[2-{p-Chlorophenyl}cyclopentyl)imino]hexahydroazepine hydrochloride

From 575 g of p-chlorophenyl bromide and 78 g of magnesium turnings in 2.6 liters of anhydrous ether was prepared p-chlorophenyl magnesium bromide to which was added dropwise a solution of 252 g of cyclopentanone in 1 liter of ether. The mixture was stirred overnight and was decomposed by careful addition of dilute hydrochloric acid. The organic phase was separated, washed and dried, and the solvent was evaporated. The resulting solid was recrystallized from ethanol to give 316 g of 1-(p-chlorophenyl)cyclopentene, M.P. 71°–73° C., which was dissolved in 2.9 liters of acetic acid containing 6 ml of concentrated sulfuric acid. To this solution 133 g of 50% hydrogen peroxide was added dropwise during which time the reaction temperature was maintained at 30° to 35° C. The reaction mixture was stirred overnight after which water was added and the product was extracted into ether. The extract was washed, dried and the solvent evaporated leaving crude 2-(p-chlorophenyl)cyclopentanone which was distilled, B.P. 135°–154° C. (0.1 mm) yielding 140 g. The oxime, M.P. 154°–155° C. was reduced using Raney nickel in alcoholic ammonia to give 2-(p-chlorophenyl)cyclopentylamine which was subsequently converted to the hydrochloride salt, M.P. 226°–228° C. Following the procedure of Example 1, only substituting for cis-2-phenylcyclopentylamine hydrochloride, an appropriate amount of 2-(p-chlorophenyl)cyclopentylamine hydrochloride, the desired product was obtained, M.P. 253°–255° C.

EXAMPLE 6

Following the procedure of Example 1, only substituting for O-methylcaprolactim an appropriate amount of O-methylenantholactim, O-methylcaprylolactim, O-methylvalerolactim or O-methyl-5-tert-butylcaprolactim, the following compounds are obtained:
octahydro-2-[(cis-2-phenylcyclopentyl)imino]azocine hydrochloride,
octahydro-2-[(cis-2-phenylcyclopentyl)imino]azonine hydrochloride, M.P. 207°–209° C.,
2-[(cis-2-phenylcyclopentyl)imino]piperidine hydrochloride, M.P. 173°–176° C.,
5-tert-butylhexahydro-2-[(cis-2-phenylcyclopentyl)imino]azepine hydrochloride, M.P. 291°–293° C.

EXAMPLE 7

Hexahydro-2-[(trans-2-phenylcyclohexyl)imino]azepine hydrochloride

Following the procedure of Example 1, only substituting for cis-2-phenylcyclopentylamine hydrochloride an appropriate amount of trans-2-phenylcyclohexylamine hydrochloride, M.P. 251°–257° C., and employing a reaction time of 38 days, the desired product was obtained, M.P. 236°–239° C.

By the procedure of Example 1, only substituting for cis-2-phenylcyclopentylamine hydrochloride an appropriate amount of the hydrochloride salt of an amine listed in Table I, the respective products listed in Table I are obtained. The amines employed in Examples 8 through 12 are described by W. F. Trager et al., in J. Org. Chem. 27, 3006–10 (1962), and those used in Examples 13 and 14 are described by M. Mousseron and M. Mousseron-Canet, C. R. Acad. Sci. 239, 502 (1954). The amines employed in Examples 15 and 16 are obtained by the reduction of 2-(m-anisyl)cyclohexanone oxime and 2-(p-anisyl)cyclohexanone oxime [W. C. and R. B. Wildman, J. Org. Chem. 17, 581 (1952)] and those used in Examples 17 and 18 are obtained by the reduction of the oxime of 2-cyclopentylcyclopentanone (H. Cristol et al., Bull. Soc. Chim. France 1958, 556).

| Ex. No. | Amine | Final Product |
|---|---|---|
| 8 | 2-o-tolyl)cyclohexylamine | hexahydro-2-[2-({0-tolyl}-cyclohexyl)imino]azepine hydrochloride |
| 9 | 2-(p-tolyl)cyclohexylamine | hexahydro-2-[2-({p-tolyl}-cyclohexyl)imino]azepine hydrochloride |
| 10 | 2-(o-chlorophenyl)cyclohexylamine | 2-[2-({o-chlorophenyl}-cyclohexyl)imino]hexahydroazepine hydrochloride |
| 11 | 2-(m-chlorophenyl)cyclohexylamine | 2-[2-({m-chlorophenyl}-cyclohexyl)imino]hexahydroazepine hydrochloride |
| 12 | 2-(p-chlorophenyl)cyclohexylamine | 2-[2-({p-chlorophenyl}-cyclohexyl)imino]hexahydroazepine hydrochloride |
| 13 | cis-2-cyclopentylcyclohexylamine | 2-[2-({cis-2-cyclopentyl}-cyclohexyl)imino]hexahydroazepine hydrochloride |
| 14 | trans-2-cyclopentylcyclohexylamine | 2-[2-({trans-2-cyclopentyl}-cyclohexyl)imino]hexahydroazepine hydrochloride |
| 15 | 2-(m-anisyl)cyclohexylamine | 2-[2-({m-anisyl}cyclohexyl)-imino]hexahydroazepine hydrochloride |
| 16 | 2-(p-anisyl)cyclohexylamine | 2-[2-({p-anisyl}cyclohexyl)-imino]hexahydroazepine hydrochloride |
| 17 | cis-2-(cyclopentyl)cyclopentylamine | 2-[1-({cis-2-cyclopentyl}-cyclopentyl)imino]hexahydroazepine hydrochloride |
| 18 | trans-2-(cyclopentyl)cyclopentylamine | 2-[2-({trans-2-cyclopentyl}-cyclopentyl)imino]hexahydroazepine hydrochloride |

EXAMPLE 19

Hexahydro-2-[(2-{2-thienyl}cyclopentyl)imino]azepine hydrochloride

By the procedure described in U.S. Pat. No. 2,520,516 (1950) 2-(2-thienyl)cyclopentylamine hydrochloride, M.P. 168°–172° C., was prepared and substituted for cis-2-phenylcyclopentylamine hydrochloride in Example 1 to give the desired product, M.P. 144°–151° C.

EXAMPLE 20 cis- and trans-Hexahydro-2-[(2-phenylcycloheptyl)imino]azepine hydrochloride

Following the procedure of Example 1 only substituting for cis-2-phenylcyclopentylamine hydrochloride an appropriate amount of cis- or trans-2-phenylcycloheptylamine hydrochloride, M.P. 229°–230° C. and 199°–201° C. respectively, and using reaction times of 20 and 21 days respectively, the desired products were obtained, cis- M.P. 234°–235° C., trans- M.P. 207°–211° C.

EXAMPLE 21

2-[(cis-2-Cyclohexylcyclopentyl)imino]piperidine hydrochloride

Following the procedure of Example 1, only substituting for cis-2-phenylcyclopentylamine hydrochloride and O-methylcaprolactim, appropriate amounts of cis-2-(cyclohexyl)cyclopentylamine hydrochloride and O-methylvalerolactim respectively the desired product was obtained. M.P. 195.5°–197° C.

EXAMPLE 22

2-[(cis-2-Phenylcyclopentyl)imino]azacyclotridecane hydrochloride

To 21.7 g of 2-azacyclotridecanone in 200 ml of dry benzene was added dropwise 15.3 g of phosphorus oxychloride. The mixture was stirred at room temperature for 4 hours after which 19.8 g of cis-2-phenylcyclopentylamine hydrochloride was added. The reaction mixture was stirred at room temperature for 2 hours and refluxed for 24 hours. The resulting homogeneous solution was washed with 2N NaOH, 2N HCl and saturated NaCl solution, dried over sodium sulfate and the solvent evaporated. The resulting oily product crystallized from acetone and was recrystallized from methanol-acetone to give the desired product, M.P. 156°–159° C.

EXAMPLE 23

By the procedure of Example 22, only substituting for 2-azacyclotridecanone an appropriate amount of N-methyl-2-pyrrolidone or 3-chlorocaprolactam the following products are obtained:
N-methyl-2-[(cis-2-phenylcyclopentyl)imino]pyrrolidine hydrochloride,
3-chloro-2-[(cis-2-phenylcyclopentyl)imino]hexahydroazepine hydrochloride.

EXAMPLE 24

O-Methylvalerolactim

To a refluxing solution of 100 g of valerolactam in 350 ml of dry benzene was added dropwise 125 g of dimethylsulfate. After refluxing overnight the mixture was treated with saturated potassium carbonate solution, dried and the solvent was evaporated. The product was distilled at 20 mm, B.P. 55°–57° C.

EXAMPLE 25

Following the procedure of Example 24 only substituting for valerolactam an appropriate amount of enantholactam, caprylolactam, 5-tert-butylcaprolactam or caprolactam the following compounds were prepared:
O-methylenantholactim, B.P. 48°–53° C. (2.0 mm),
O-methylcaprylolactim, B.P. 44°–46° C. (0.5 mm),
O-methyl-5-tert-butylcaprolactim, B.P. 76°–79° C. (0.4–2.3 mm),
O-methylcaprolactim, B.P. 60°–65° C. (13.0 mm).

EXAMPLE 26

2-(Hexahydroazepin-2-ylidenamino)-1-phenylcyclopentanol hydrochloride

A solution of 73.5 g (0.75 mole) of 1,2-cyclopentanedione in 400 ml of ether was added to 1.5 moles of phenyl lithium in 1.2 liter of ether, and the mixture was stirred under $N_2$ for one half hour. After careful addition of water, the ethereal layer was separated, dried over magnesium sulfate and the solvent evaporated. The residue was distilled under reduced pressure and gave 77.2 g of 2-hydroxy-2-phenylcyclopentanone, b.p. 122°–126° C. (1.5 mm), $n_D^{25}$ 1.5551. The oxime was prepared by known procedures, m.p. 110°–112° C., and was reduced by hydrogenation over Raney nickel in 20% alcoholic ammonia. Removal of catalyst, evaporation of solvent and addition of HCl gave 2-hydroxy-2-phenylcyclopentylamine hydrochloride, m.p. 198°–199° C.

Following the procedure described in Example 1, only substituting for cis-2-phenylcyclopentylamine hydrochloride an appropriate amount of 2-hydroxy-2-phenylcyclopentylamine hydrochloride and employing a reaction time of 47 days the desired product was obtained, M.P. 261°–262° C.

EXAMPLE 27

5-Methyl-2-[(2-phenylcyclopentyl)imino]pyrrolidine hydrochloride

A slurry of 3.0 g (0.0152 mole) of powdered 2-phenylcyclopentylamine hydrochloride and 3 ml of 5,O-dimethylbutyrolactim is allowed to stand at room temperature for 6 days with occasional stirring during which time sufficient ethanol is added to maintain the slurry. The slurry is then cooled to −20° C., and after about four hours a precipitate forms. The precipitate is collected and recrystallized several times from acetone-methanol to give 5-methyl-2-[(2-phenylcyclopentyl)imino]pyrrolidine hydrochloride, M.P. 175°–178° C.

EXAMPLE 28

2-[(2-Phenylcyclopentyl)imino]pyrrolidine hydrochloride

A slurry of 3.0 g (0.0152 mole) of powdered 2-phenylcyclopentylamine hydrochloride and 3 ml of O-methylbutyrolactim is allowed to stand at room temperature with occasional stirring for 6 days after which the material is covered with absolute ether. The solution is allowed to stand at room temperature for an additional 6 days. A precipitate forms which is collected and recrystallized from acetone-methanol and dried to give 2-[(2-phenylcyclopentyl)imino]pyrrolidine hydrochloride, M.P. 155°–158° C.

EXAMPLE 29

5-Methyl-2-[(cis-2-cyclohexylcyclopent-1-yl)imino]pyrrolidine hydrochloride

When in the procedure of Example 27, 3.0 g (0.0147 mole) of 1-cyclohexylcyclopentylamine hydrochloride is substituted for 1-phenylcyclopentylamine, and the slurry is allowed to stand at room temperature for 8 days, 5-methyl-2-[(cis-2-cyclohexylcyclopent-1-yl)imino]pyrrolidine hydrochloride is obtained, M.P. 234°–236° C. (dec).

EXAMPLE 30

2-[(cis-2-cyclohexylcyclopent-1-yl)imino]pyrrolidine hydrochloride

A slurry of 3.0 g (0.0147 mole) of powdered 1-cyclohexylcyclopentylamine hydrochloride and 3 ml of O-methylbutyrolactim is allowed to stand at room temperature for 8 days during which time sufficient ethanol is added to maintain a slurry. A precipitate forms which is collected, washed with ether, dried and recrystallized from acetone-methanol to give 2-[(cis-2-cyclohexylcyclopent-1-yl)imino]pyrrolidine hydrochloride, M.P. 227°–228° C.

EXAMPLE 31

1-Benzyl-2-[(cis-2-phenylcyclopentyl)imino]pyrrolidine hydrochloride

To 26.3 g (0.15 mole) of N-benzylbutyrolactone in 200 ml of dry benzene is added dropwise 19.2 g (0.125 mole) of phosphorus oxychloride. The mixture is stirred at room temperature for four hours after which 24.7 g (0.125 mole) of 1-phenylcyclopentylamine hydrochloride is added, and stirring is continued at room temperature for two hours. The reaction mixture is refluxed for 24 hours and then allowed to stand at room temperature for five days. A solid forms which is separated and the filtrate is washed with 2N HCl. The wash and solid residue are made basic with 2N sodium hydroxide solution, extracted into ether and dried over sodium sulfate to give 40.3 g of an oil. To the oil in acetone is added one equivalent of methanolic HCl. A precipitate forms which is recrystallized from methylene chloride-ether to give 1-benzyl-2-[(cis-2-phenylcyclopentyl)imino]pyrrolidine hydrochloride, M.P. 158°–166° C.

EXAMPLE 32

An illustrative composition for tablets is as follows:

|  | Per Tablet |
|---|---|
| (a) 2-[(2-cyclohexylcyclopentyl)imino]hexahydroazepine hydrochloride | 100 mg |
| (b) Wheat Starch | 15 mg |
| (c) Lactose | 33.5 mg |
| (d) Magnesium stearate | 1.5 mg |

A granulation obtained upon mixing lactose with the starch and granulated starch paste is dried, screened and mixed with the active ingredient and magnesium stearate. The mixture was compressed in tablets weighing 150 mg each.

In a similar manner other compositions may be prepared by substituting the other compounds of this invention for 2-[(2-cyclohexylcyclopentyl)imino]hexahydroazepine used in this example.

We claim:
1. A compound selected from
(A) a compound of the formula

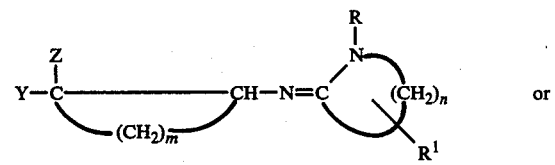

(B) a pharmaceutically acceptable acid addition salt thereof, wherein Y is selected from the group consisting of phenyl or substituted phenyl wherein the substituents on the substituted phenyl are selected from the group consisting of halogen, lower alkyl of from 1 to 4 carbon atoms or lower alkoxy of from 1 to 4 carbon atoms; Z is hydrogen; R is selected from the group consisting of hydrogen, lower alkyl of from 1 to 4 carbon atoms, phenyl or benzyl; $R^1$ is selected from the group consisting of hydrogen, halogen or lower alkyl of from 1 to 4 carbon atoms, $m$ is an integer of from 3 to 6; and $n$ is an integer of from 3 to 11.

2. A compound of claim 1 where $m$ is 3 to 5, $n$ is 4 to 7 and R and $R^1$ are each hydrogen.

3. A compound of claim 2 which is hexahydro-2-[(2-phenylcyclopentyl)imino]azepine or a pharmaceutically acceptable acid addition salt thereof.

4. A compound of claim 2 which is hexahydro-2-[(2-phenylcycloheptyl)imino]azepine or a pharmaceutically acceptable acid addition salt thereof.

5. A compound of claim 2 which is 2-[(2-phenylcyclopentyl)imino]piperidine or a pharmaceutically acceptable acid addition salt thereof.

6. A compound of claim 2 which is octahydro-2-[(2-phenylcyclopentyl)imino]azonine or a pharmaceutically acceptable acid addition salt thereof.

7. A compound of claim 2 which is 2-[(cis-2-phenylcyclopentyl)imino]azacyclotridecane or a pharmaceutically acceptable acid addition salt thereof.

* * * * *